(12) United States Patent
Dadisman

(10) Patent No.: US 8,100,893 B2
(45) Date of Patent: Jan. 24, 2012

(54) LASER CATHETER CALIBRATOR

(75) Inventor: Tom Dadisman, Arvada, CO (US)

(73) Assignee: The Spectranetics Corporation, Colorado Springs, CO (US)

( * ) Notice: Subject to any disclaimer, the term of this patent is extended or adjusted under 35 U.S.C. 154(b) by 280 days.

(21) Appl. No.: 11/946,376

(22) Filed: Nov. 28, 2007

(65) Prior Publication Data

US 2009/0299351 A1    Dec. 3, 2009

(51) Int. Cl.
*A61B 18/24*    (2006.01)

(52) U.S. Cl. .......................... 606/15; 128/898; 600/118

(58) Field of Classification Search ............. 606/15; 600/117, 118; 128/898

See application file for complete search history.

(56) References Cited

U.S. PATENT DOCUMENTS

| | | | |
|---|---|---|---|
| 4,611,270 A | 9/1986 | Klauminzer et al. | |
| 4,641,912 A | 2/1987 | Goldenberg | |
| 4,650,327 A * | 3/1987 | Ogi ........................... | 356/243.1 |
| 4,732,448 A | 3/1988 | Goldenberg | |
| 4,941,308 A | 7/1990 | Grabenkort et al. | |
| 4,962,502 A | 10/1990 | Adams | |
| 4,981,355 A | 1/1991 | Higgins | |
| 4,998,794 A | 3/1991 | Holzman | |
| 5,016,964 A | 5/1991 | Donnelly | |
| 5,128,601 A | 7/1992 | Orbach et al. | |
| 5,151,909 A | 9/1992 | Davenport et al. | |
| 5,365,925 A | 11/1994 | Lee | |
| 5,383,199 A | 1/1995 | Laudenslager et al. | |
| 5,456,680 A | 10/1995 | Taylor et al. | |
| 6,615,062 B2 | 9/2003 | Ryan et al. | |
| 7,268,684 B2 | 9/2007 | Tethrake et al. | |
| 7,568,619 B2 | 8/2009 | Todd et al. | |
| 7,934,648 B2 | 5/2011 | Charles et al. | |
| 7,988,633 B2 | 8/2011 | Hossack et al. | |
| 2002/0128685 A1 | 9/2002 | Hoium et al. | |
| 2003/0097048 A1 * | 5/2003 | Ryan et al. ................ | 600/309 |
| 2003/0195402 A1 * | 10/2003 | Fein et al. .................. | 600/323 |
| 2005/0261551 A1 * | 11/2005 | Couvillon .................. | 600/118 |
| 2005/0272975 A1 * | 12/2005 | McWeeney et al. ........ | 600/113 |
| 2006/0155348 A1 * | 7/2006 | deCharms ................... | 607/89 |
| 2009/0221919 A1 * | 9/2009 | Ben Dor et al. ............ | 600/473 |

OTHER PUBLICATIONS

Bennett et al., "Variable Laser Attenuators—Old and New," Laser Focus, Apr. 1983, vol. 19(4), pp. 55-62.

* cited by examiner

*Primary Examiner* — Henry M Johnson, III
*Assistant Examiner* — Jeffrey B Lipitz
(74) *Attorney, Agent, or Firm* — Scott J. Hawranek; Sheridan Ross, P.C.

(57) ABSTRACT

A catheter assembly is disclosed according to one embodiment of the invention. The assembly includes a catheter body, a housing and a detector. The catheter includes a distal tip, a proximal end, and a fiber optic extending between the proximal end and the distal tip. The housing may include a channel adapted to support at least a portion of the distal tip of the catheter. The may be detector disposed within the housing so as to be spaced a fixed distance from the distal tip of the catheter. Methods for providing and calibrating a catheter supported within housing are also disclosed according to other embodiments of the invention.

24 Claims, 12 Drawing Sheets

LASER CATHETER CALIBRATOR

BACKGROUND OF THE INVENTION

This disclosure relates in general to laser catheters and, but not by way of limitation, to laser catheter calibration among other things.

Laser catheters are often calibrated prior to use in order to regulate the fluence and/or the repetition rate of the laser catheter. A user may calibrate a laser catheter by holding the tip of a catheter near an energy detector connected with the catheter system. Having a user hold the catheter near an energy detector may introduce calibration errors by presenting individual variations. Different individuals may hold the catheter at different positions relative to the energy detector and may not hold the catheter steady during the calibration process. Moreover, potential calibration errors may occur if a user does not properly follow calibration procedures. Furthermore, catheters also are sterilized prior to use and as such the person performing the hand-held calibration procedure must exercise sterility protocols.

Accordingly, there is a need in the art for improved laser catheter calibrator and/or calibration procedures.

BRIEF SUMMARY OF THE INVENTION

A catheter is disclosed according to one embodiment of the invention. The catheter may include a catheter body including a distal tip, a proximal end, and a fiber optic extending between the proximal end and the distal tip. The catheter may be supported within a channel of a housing. The channel may be adapted to receive and support at least a portion of the distal tip of the catheter body at a fixed distance from a detector. The channel is also adapted to provide a sterile environment for the distal tip of the catheter. Both the catheter and the housing may be sterilized before or after the distal tip is inserted into the channel. The catheter distal tip may be supported a specific distance from the detector within the channel, for example, the catheter may be supported, for example, approximately ¼, ½, ¾, 1¼, 1½, 1¾, 2, 2¼, 2½, 2¾, or 3 inches from the detector. The proximal end of the catheter may include a connector that is designed to optically connect with a laser.

A calibration method is also disclosed according to another embodiment of the invention. The method includes providing a catheter with the distal tip of the catheter supported within a housing. The housing may include a channel and a detector. The channel may support the distal tip of the catheter at a fixed distance from the detector. The catheter, channel, and/or housing may be sterilized together or separately. Moreover, the catheter within the housing may be packaged within a sterile packaging and provided to a consumer. The proximal end of the catheter may be coupled with a laser and calibrated. The calibration may include pulsing the laser with fixed parameters and detecting laser light from the distal tip of the catheter at the detector. The pulsing may end when/if the detector detects light that is of a significantly strong signal, at or above a threshold value or within pre-selected or pre-entered parameters defined by the catheter type. If the detected light is not sufficient the operating parameters of the laser may be adjusted and pulsed until the detected light reaches the threshold value. In another embodiment, if the detected light is not within pre-selected or pre-entered parameters the calibration fails.

A method for providing a sterile catheter to a customer is provided according to another embodiment of the invention. The method may include providing a housing that includes a channel and a detector and placing at least the tip of a sterilized catheter within the channel. The channel, catheter tip and/or housing may be sterile. The channel may be adapted to keep the tip of the catheter sterilized at least until the tip is removed from the channel. The channel may be adapted to support the catheter a fixed distance from the detector. The catheter and housing may be provided to a customer within a sterile package.

The method may also include calibrating the catheter with a laser. Calibration may include coupling the catheter with a laser and pulsing the laser with fixed operating parameters. Light may then be detected at the detector and compared with a threshold value. If the detected light is greater than or equal to a threshold value and/or within pre-entered or pre-selected parameters defined by the user or the catheter type, the calibration stops. These pre-entered parameters may be found within a look-up table. For example, the laser may receive an indication of the type of catheter inserted within the channel from the catheter or from a user through the user interface. Pre-entered parameters for the specific catheter may then be found with the look-up table and used to calibrate the catheter. Otherwise the operating parameters may be adjusted and pulsed until the detected light is at or within 1%, 5%, or 10% of the threshold value.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

In the appended figures, similar components and/or features may have the same reference label. Where the reference label is used in the specification, the description is applicable to any one of the similar components having the same reference label.

DETAILED DESCRIPTION OF THE INVENTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It being understood that various changes may be made in the function and arrangement of elements without departing from the spirit and scope as set forth in the appended claims.

In one embodiment, the present disclosure provides for a catheter supported within a housing. The housing, for example, may include a channel and a detector. The catheter may be supported within the channel such that the tip of the distal tip of the catheter is a fixed distance from the detector. Moreover, the distal tip of the catheter and/or the channel may be sterilized prior to placing the distal tip of the catheter within the channel. The distal tip of the catheter may remain sterile while supported by the channel within the housing. Thus, the catheter may be sterilized, packaged, and provided to a user. The housing and catheter may be coupled together and then sterilized according to another embodiment of the invention. The user may then have a catheter that may be used without requiring sterilizing of the catheter prior to use. The catheter and housing may also be disposable.

Prior to operation and while the catheter is supported within the channel of the housing, the catheter may be calibrated. The proximal end of the catheter may be optically connected with a laser, for example, an excimer laser. The laser may the be operated or pulsed. The laser may be operated in response to receiving an indication from a user through a user interface, for example, through a button, switch, keyboard, mouse, pointer, touch screen, etc. The user may also input laser operation parameters as well as calibration threshold parameters. During operation of the laser, the detector may detect laser light from the catheter. The detected light may be compared with a threshold value. If the detected laser light has a sufficient signal based on a comparison with a threshold value, the calibration may be complete. The laser may the be pulsed using different operating parameters and calibrated with these parameters.

Figure 1:
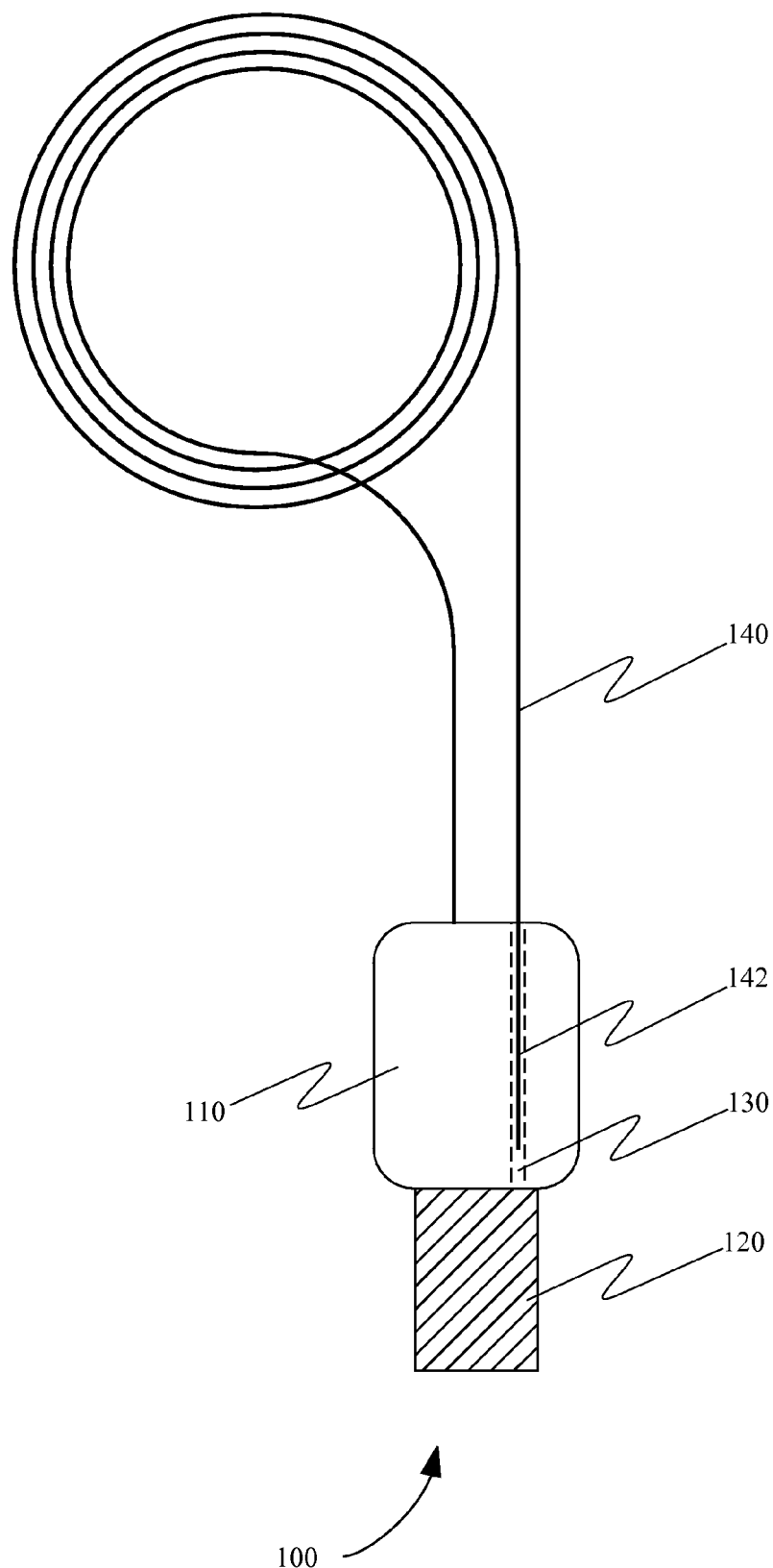
FIG. 1 shows an exemplary laser catheter according to one embodiment of the invention.

Referring first to FIG. 1, a catheter is shown according to one embodiment of the invention. A catheter 140 is shown with a long fiber optic section between a distal tip 142 and a proximal end that is secured to a housing 110. The housing 110 includes a connector 120 that is used to couple the catheter to a laser system. The distal tip 142 of the catheter 140 is secured within a channel 130 of the catheter housing 110. The channel 130 is shown as a slot or tube within the catheter housing 110. The catheter 140 may include a fiber optic that channels light through the catheter and through the distal tip 142 of the catheter. An exemplary catheter 140 is described in U.S. Pat. No. 5,456,680 issued 10 Oct. 1995, entitled "Fiber optic catheter with shortened guide wire lumen," which is incorporated herein by reference in its entirety for all purposes.

Figure 2:
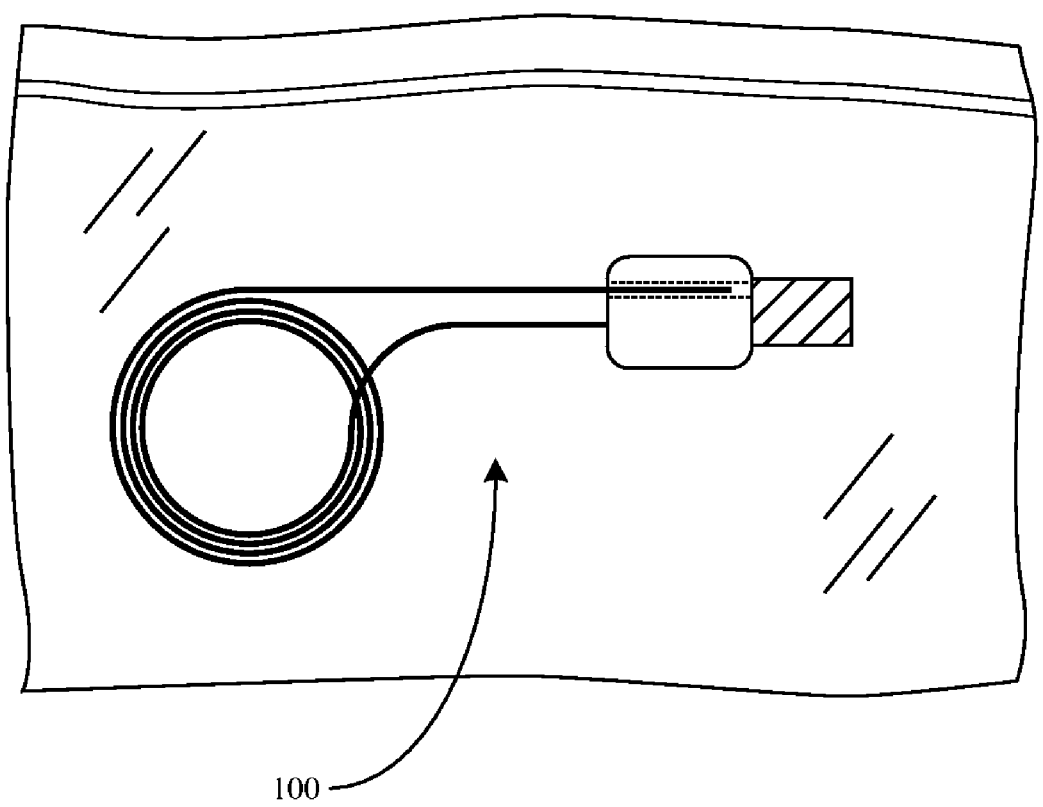
FIG. 2 shows an exemplary laser catheter within a sterilized package according to one embodiment of the invention.

The distal tip of the catheter 142 may be detachable from the catheter 140. The distal tip of the catheter 142 may be replaced with another sterile distal tip of a catheter 142. Prior to supporting the distal tip of the catheter 142 within the channel 130, the channel 130, the housing, 110 and/or catheter 140 may be sterilized. As shown in FIG. 2, the housing 110 and catheter 140 may then be packaged in a sterile package 210 and provided to a user. The package 210 may be a sterilized bag of any type. Because the catheter and/or housing have been sterilized the user may use the catheter without first sterilizing the catheter.

Figure 3:
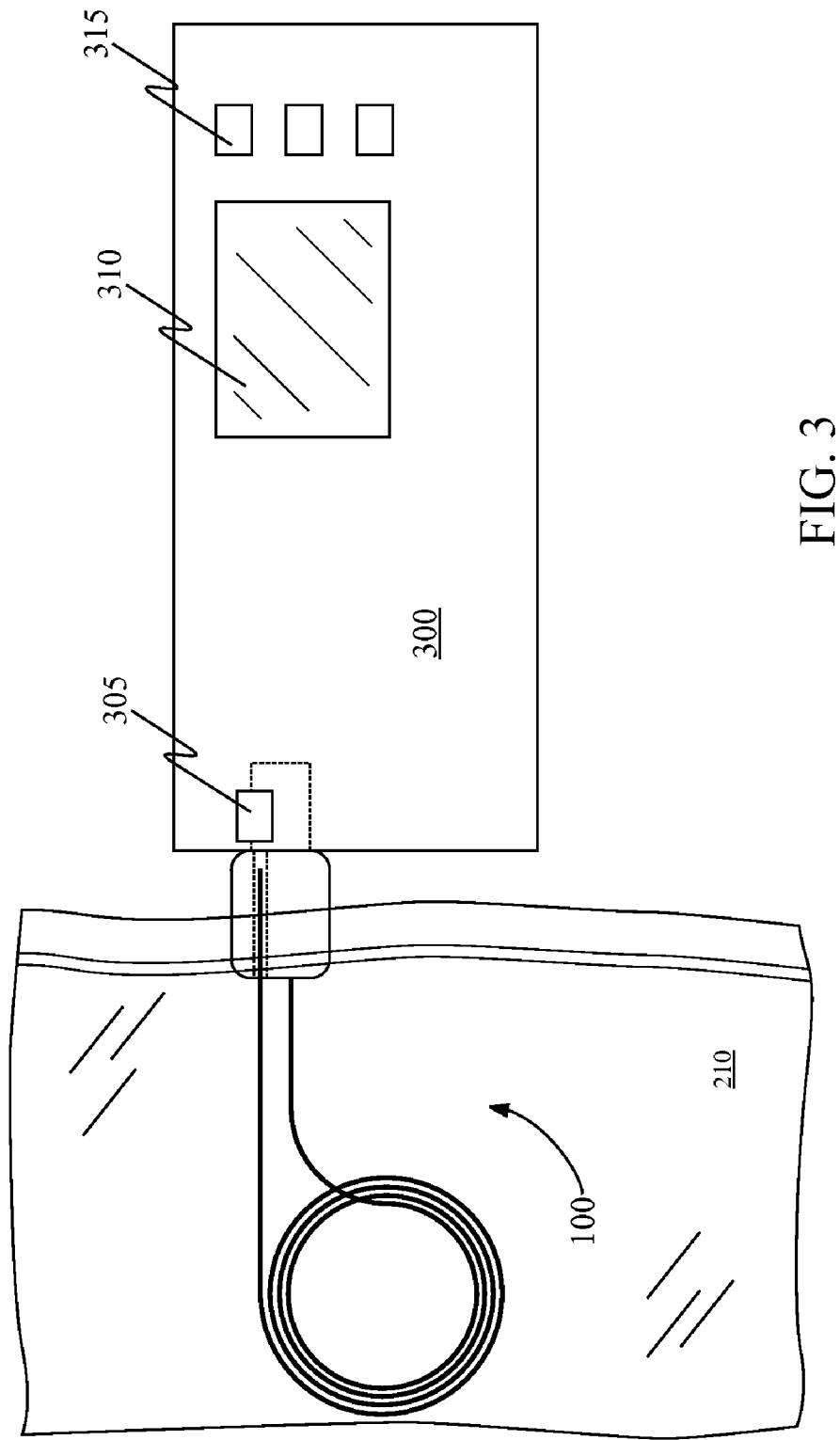
FIG. 3 shows an exemplary laser catheter coupled with a laser system according to one embodiment of the invention.

The catheter 140 and housing 110 may be coupled with a laser 300 as shown in FIG. 3 according to another embodiment of the invention. The laser 300 may be optically connected with the catheter 140 through the connector 120 and may transmit light through the fiber optic portion of the catheter 140. As shown, the catheter 140 may be coupled with the laser system 300 while partially secured within the package 210, thus preserving sterilization. The laser system 300 may also include a detector 305. When the catheter 140 is coupled with the laser system 300, the distal tip 142 of the catheter 140 may be secured a fixed distance from the detector 305. The distal tip of the catheter 142 may be positioned one inch from the detector. In other embodiments the distal tip of the catheter may be positioned approximately ¼, ½, ¾, 1¼, 1½, 1¾, 2, 2¼, 2½, 2¾, or 3 inches from the detector. In another embodiment, the distal tip of the catheter is secured less than four inches from the detector but is not touching the detector. The laser system 300 may also include a user interface 305, 310.

In one embodiment of the invention, the proximal end of the catheter may be connected with the laser. For example, the laser may be an excimer laser operating in the ultraviolet range. The laser may produce laser light at 308 nm. Other laser types of lasers may also be used depending on the specific needs of the user and may produce laser light at various other wavelengths of light. Those skilled in the art will recognize that any type of laser may be used without deviating from the spirit and scope of the present invention. The detector 305 may include, for example, a pyroelectric sensor.

The channel 130 may comprise an elongated hollow tube that supports and/or secures the distal tip of the catheter 142 near the detector 305. The channel 130 may include detents, ridges, rings, discs, risers, etc. that may be used to support and/or secure the distal tip of the catheter 142. The distal tip of the catheter may also include flanges, detents, rings, discs, etc. that may also be used to support and/or secure the distal tip of the catheter 142 near the detector within the channel 130. Moreover, physical features of the distal tip of the catheter 142 may match and/or interact with corresponding physical features of the channel 130 to secure the distal tip of the catheter 142 with the channel 130.

Figure 4:
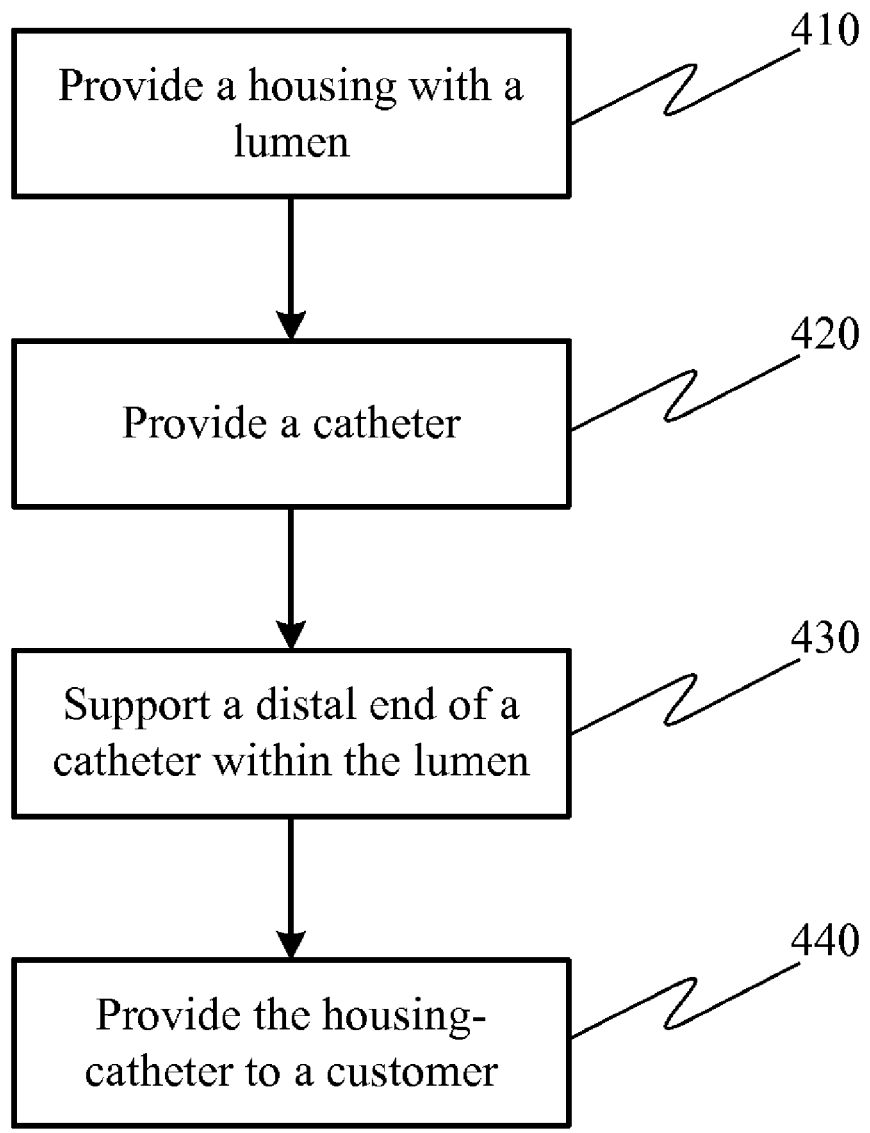
FIG. 4 shows an exemplary method for providing a sterile catheter supported within a housing to a customer according to one embodiment of the invention.

FIG. 4 shows an exemplary method for providing a sterile catheter supported within a housing to a customer according to one embodiment of the invention. A housing with a channel may be provided at block 410. As mentioned above, the housing and/or channel may be sterilized. A catheter may also be provided at block 420. The catheter may also be sterilized in whole or in part, for example, the distal tip of the catheter or the tip of the catheter may be sterilized.

The distal tip of the catheter may then be supported within a housing at block 430. The housing may support the distal tip of the catheter using a channel and/or a sheath at a fixed distance. The housing and catheter may then be packaged within a sterile package. The housing and catheter may be provided to a customer at block 440. The catheter and housing may be disposable.

Figure 5:
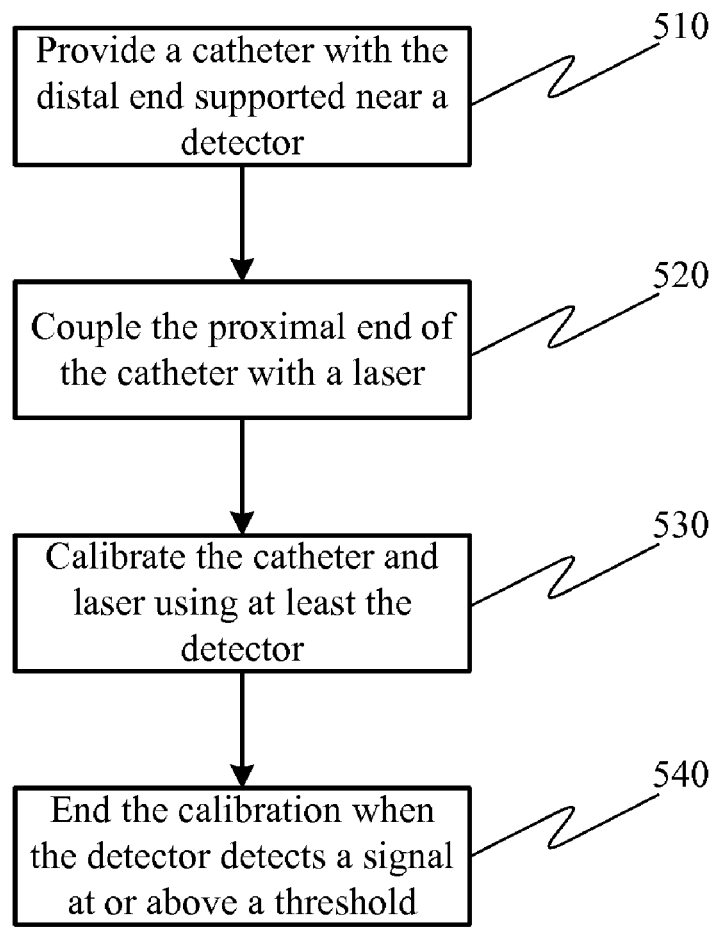
FIG. 5 shows an exemplary method for calibrating a catheter supported within a housing according to one embodiment of the invention.

FIG. 5 shows an exemplary method for calibrating a laser and catheter according to one embodiment of the invention. The distal tip of a catheter may be provided and supported near a detector within a housing at block 510. The proximal end of the catheter may be optically connected with a laser at block 520. The laser-catheter combination may then be calibrated at block 530. The calibration may be started in response to an indication received from a user through a user interface to start the calibration. The user may also enter calibration parameters such as laser operating parameters and/or calibration threshold parameters through the user interface. The calibration may end when the detector detects light at, near, or above a threshold value at block 540. For example, light within 1%, 5% or 10% of the threshold value may work. During this calibration, the distal tip of the catheter remains supported at a fixed distance from the detector within the channel.

Figure 6:
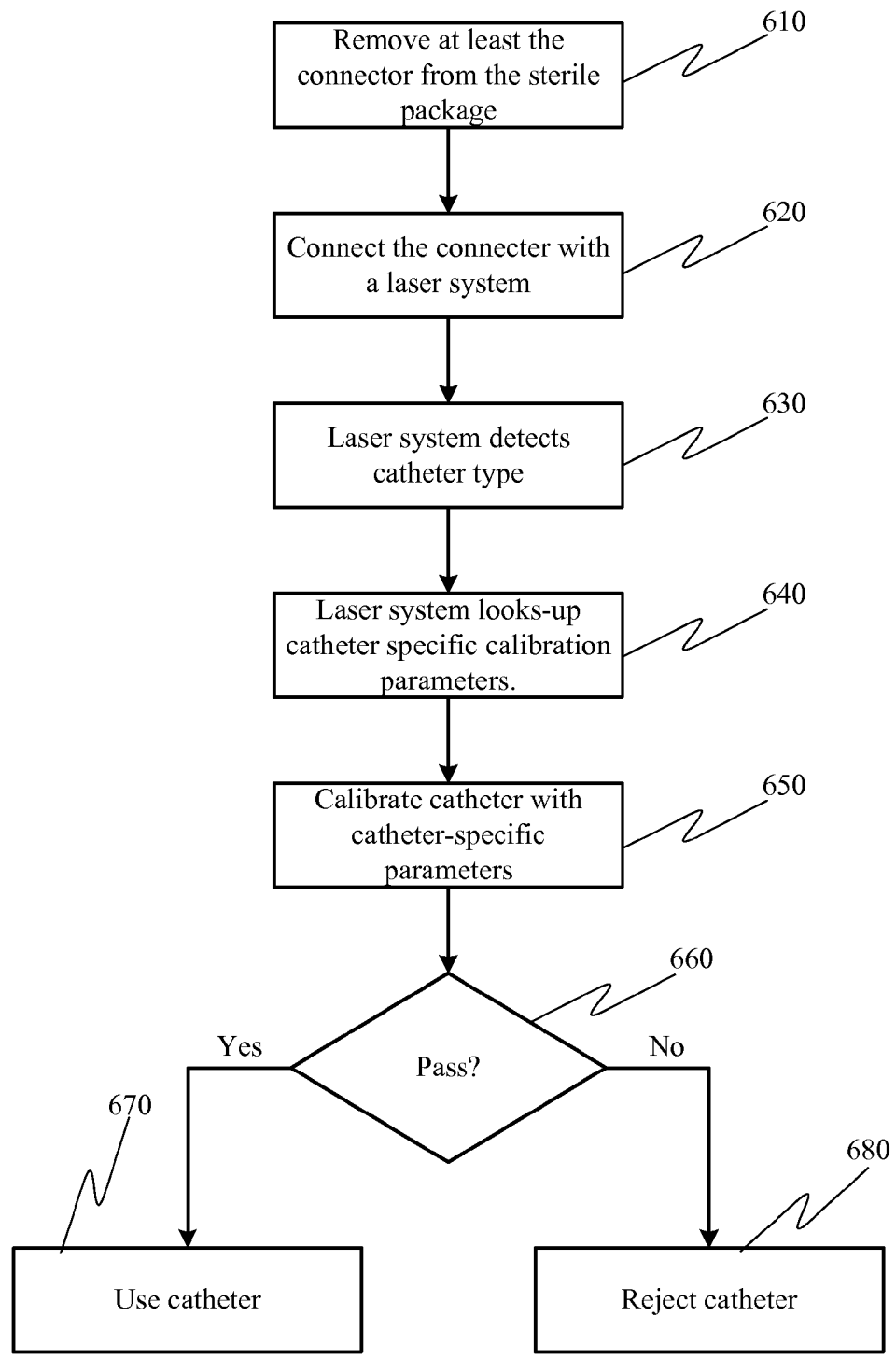
FIG. 6 shows another exemplary method for calibrating a catheter according to another embodiment of the invention.

FIG. 6 shows another exemplary method for calibrating a catheter according to another embodiment of the invention. A user, such as a doctor, nurse or assistant is provided with a catheter sterilized and placed within a sterile package. The user removes at least the connector from the package at block 610 and connects the connector with the laser system at block 620. While the connector may be partially removed when connected with the laser system, a length of the catheter may remain with the package as shown in FIG. 3. Returning to FIG. 6, the laser system may detect the type catheter inserted at block 630 and then look up the catheter-specific calibration parameters used for the specific catheter at block 640. A calibration sequence may then be performed at block 650. For example, during calibration, the laser may fire, for example, for 100 pulses. As another example, the laser may fire between 10 and 500 pulses. During this operation, the detector detects the light incident from the tip of the catheter. The system then determines whether the received energy is within the catheter specific parameters at block 660. For example, various catheters the calibration parameters may include measuring the received energy, the threshold of which may be in the range of 5 mJ to 100 mJ. These values may vary depending on the type of catheter, type or procedure or may even be manually input by a physician. If the calibration passes, the catheter may be used at block 670. If the calibration fails, then the catheter is rejected at block 680. During calibration the user may or may not be present; there is no need for the user to hold the catheter in place to ensure the catheter remains sterile as most of the catheter is within a sterile package. That is, the user may attend to other matters during calibration. An indication may occur through the laser system user interface whether the calibration has passed of failed.

Figure 7:
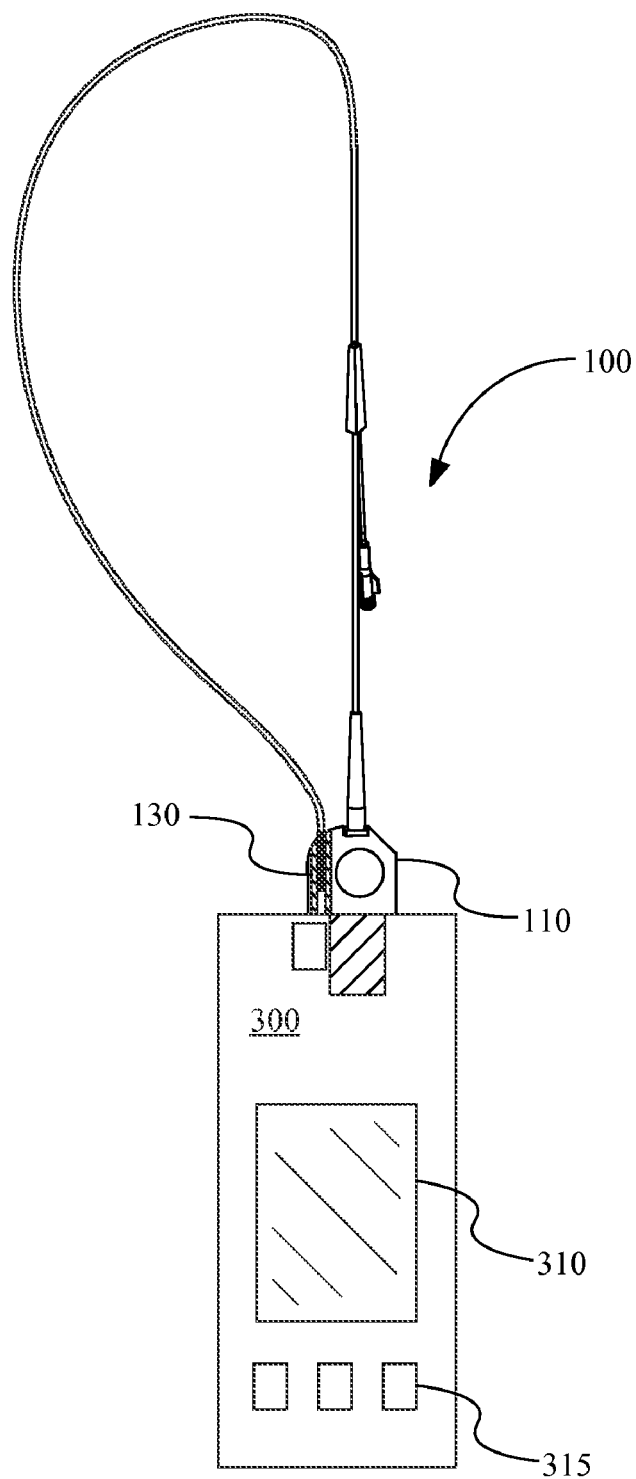
FIG. 7 shows a laser catheter coupled with a laser according to one embodiment of the invention.

FIG. 7 shows a laser catheter 100 coupled with a laser 300 according to one embodiment of the invention. The housing 100 is coupled with laser such that the lower portion of the housing is inserted within the laser. Note that the distal tip of the laser catheter 100 is secured within a channel 130 within the housing 100 in such away as to be near a calibration sensor 305.

Figure 8:
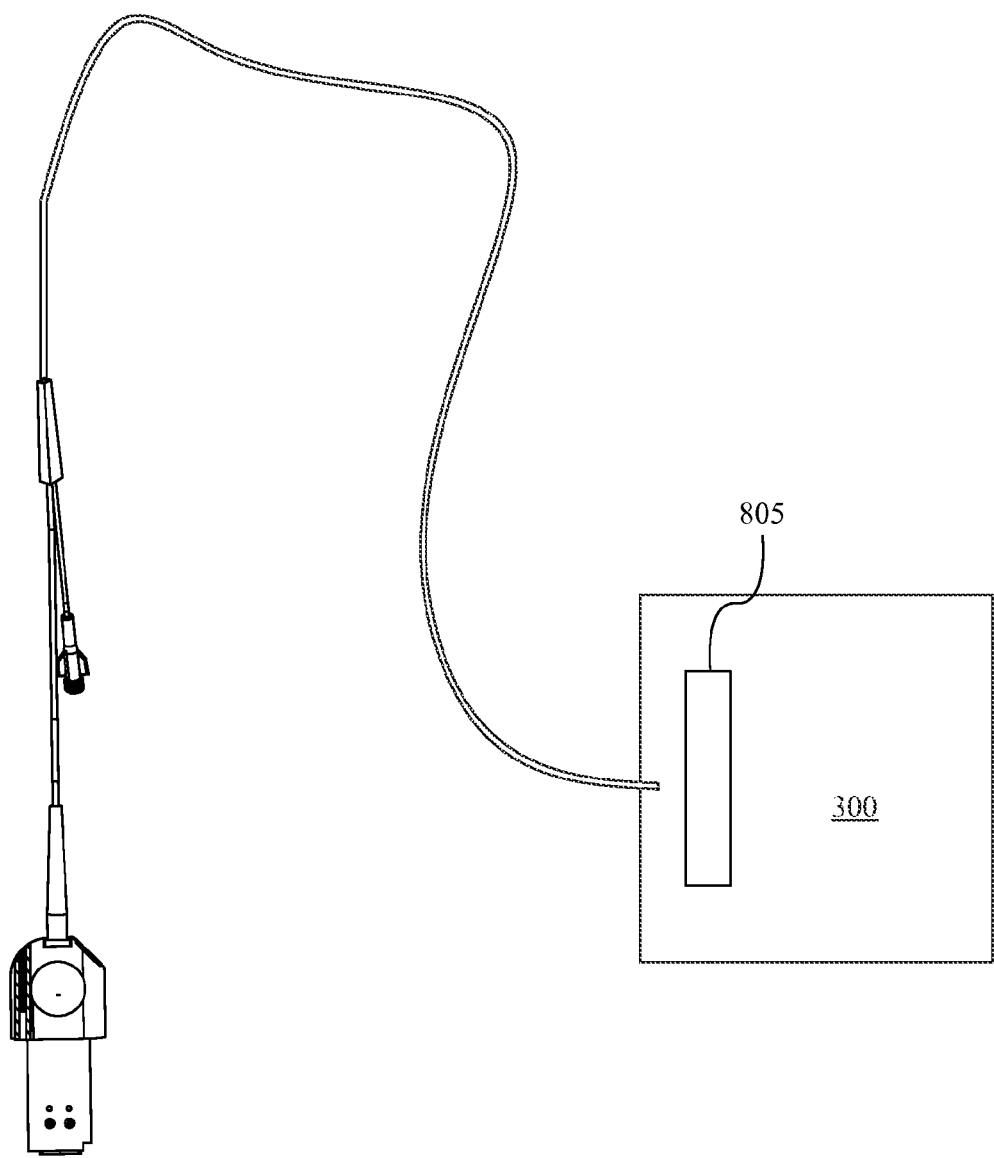
FIG. 8 shows a laser catheter with the distal tip of the catheter held near a manual calibrator.

FIG. 8 shows a laser catheter with the distal tip of the catheter held near a manual calibrator. Shows the distal tip of the catheter positioned near an external calibration sensor. In some cases, the distal tip of the catheter may be manually held near the calibration sensor.

Figure 9:
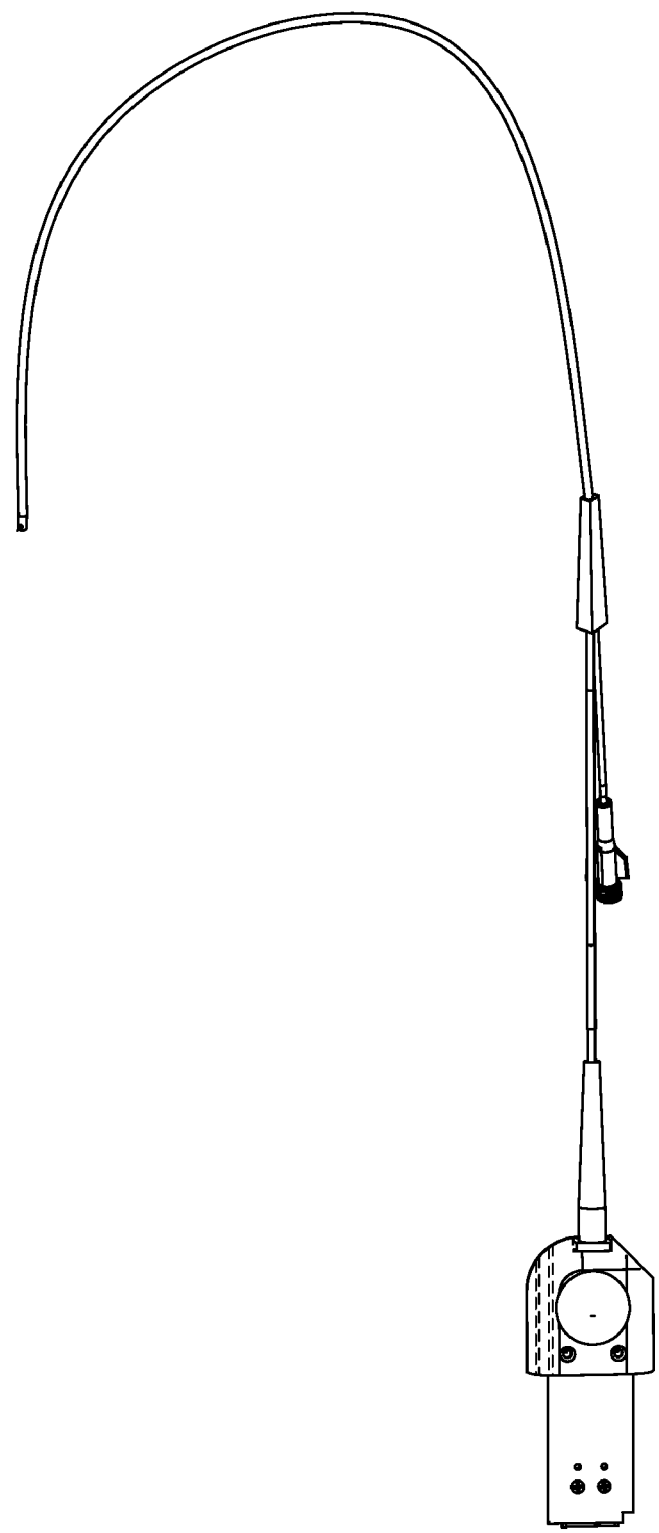
FIG. 9 shows a laser catheter according to one embodiment of the invention.

FIG. 9 shows an exemplary laser catheter.

Figure 10:
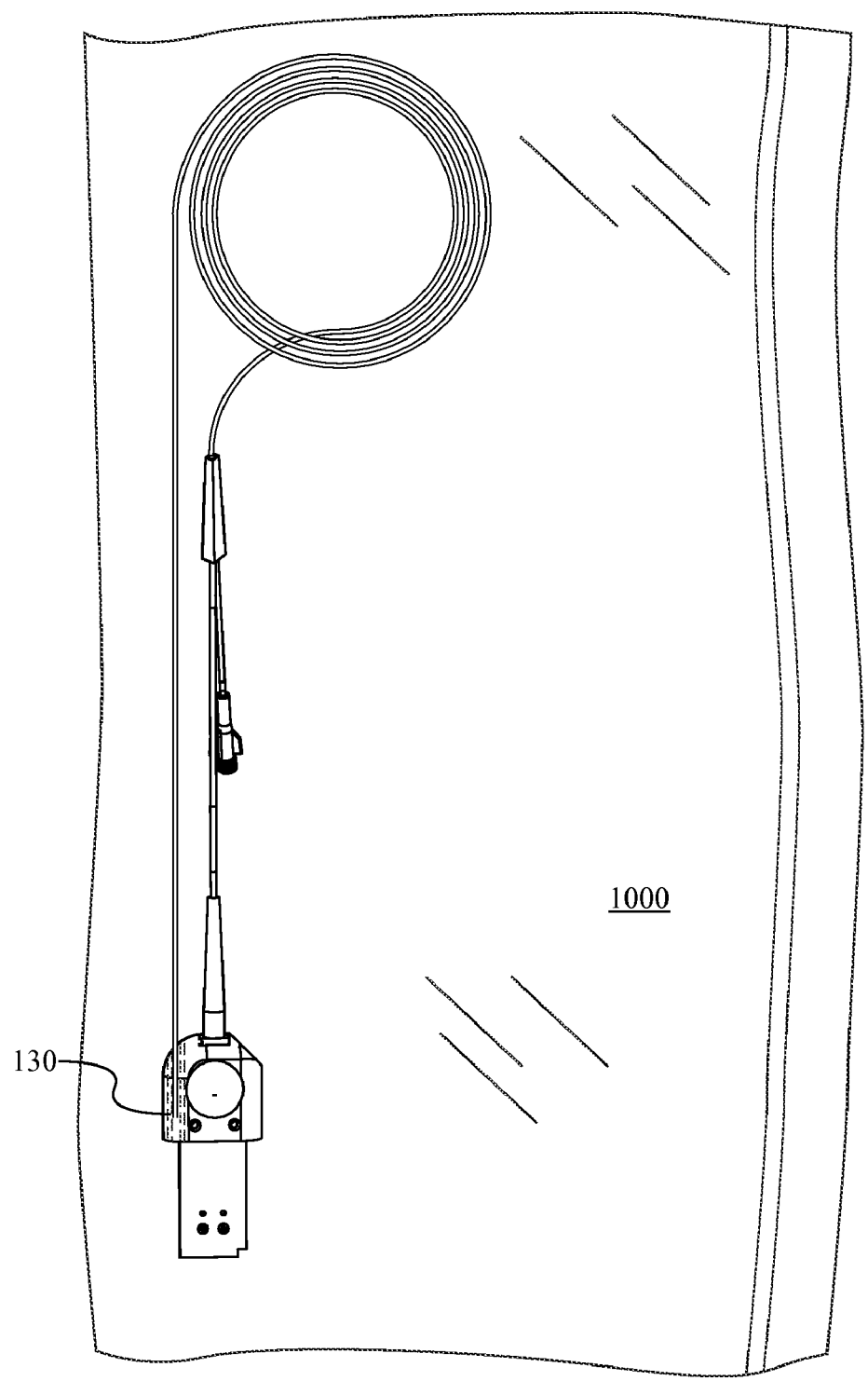
FIG. 10 shows a laser catheter secured within a sterile bag and with the distal tip of the laser catheter secured within the channel according to one embodiment of the invention.
Figure 11:
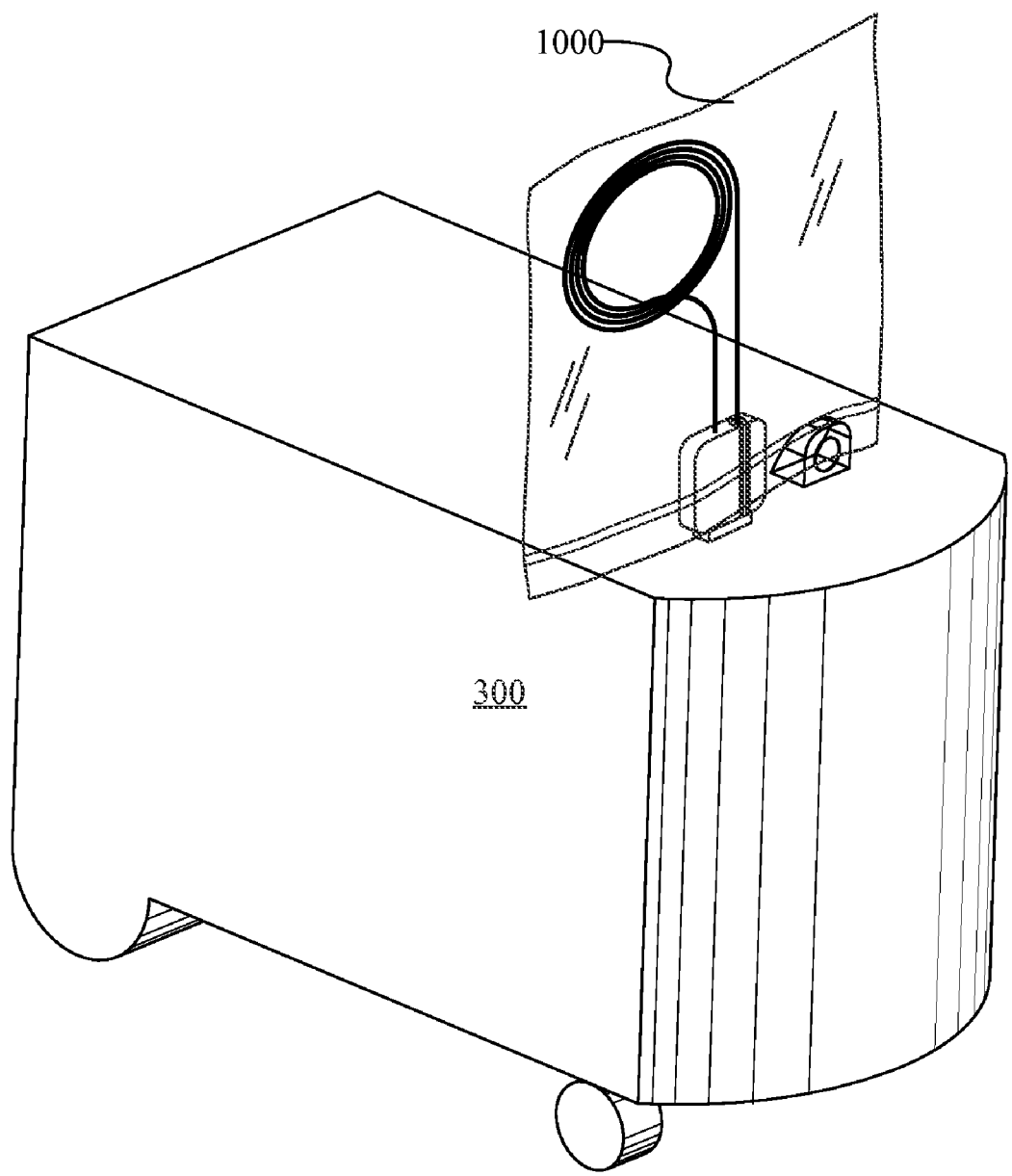
FIG. 11 shows a laser catheter secured within a sterile bag, with the distal tip of the laser catheter secured within the channel and the housing of the laser catheter coupled with the laser according to one embodiment of the invention.
Figure 12:
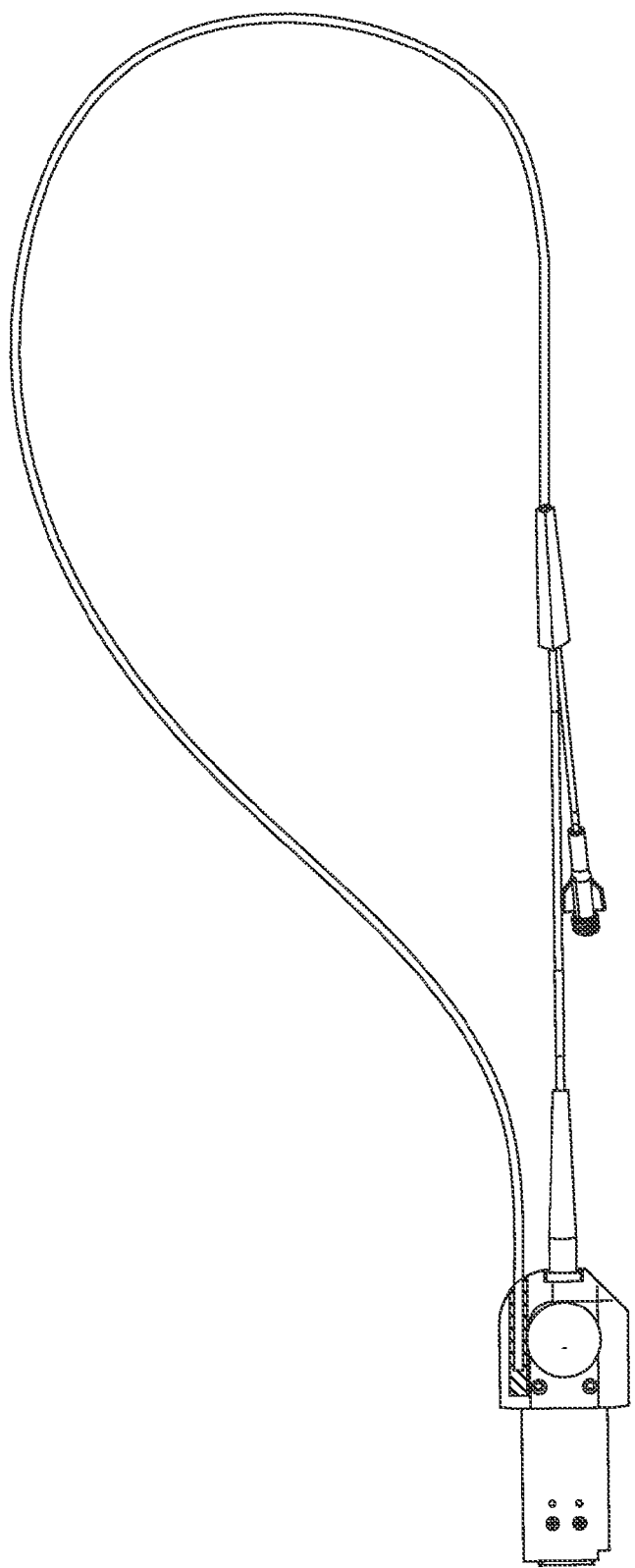
FIG. 12 shows a laser catheter with the distal tip of the laser catheter secured within the channel according to one embodiment of the invention.

FIG. 10 shows a laser catheter secured within a sterile bag 1000 and with the distal tip of the laser catheter secured within channel 130 according to one embodiment of the invention. The laser catheter may be shipped in this configuration and may be sterilized prior to packaging. FIG. 11 shows a laser catheter secured within a sterile bag 1000, with the distal tip of the laser catheter secured within the channel and the housing of the laser catheter coupled with the laser 300 according to one embodiment of the invention. As shown, the laser catheter may be calibrated within the sterile packaging by simply removing the housing and connecting the laser catheter to the laser 300 while the remaining portions of the laser catheter remain within the sterile package. FIG. 12 shows a laser catheter with the distal tip of the laser catheter secured within the channel according to one embodiment of the invention.

While the principles of the disclosure have been described above in connection with specific apparatuses and methods, it is to be clearly understood that this description is made only by way of example and not as limitation on the scope of the disclosure.

What is claimed is:

1. A method of calibrating a laser catheter, comprising:
receiving the laser catheter within a sterile package, wherein the laser catheter includes a catheter body with a distal tip, a proximal end, and a fiber optic extending between the proximal end and the distal tip and wherein the proximal end includes a housing coupled to a connector;
removing at least a portion of the connector from the package;
coupling the connector with a laser system;
coupling the distal tip of the catheter to a portion of the housing;
positioning the distal tip of the catheter a fixed distance from a light detector disposed within the laser system, wherein the distal tip of the catheter and the light detector are optically aligned; and
calibrating the catheter according to a calibration sequence, wherein the calibrating includes activating the laser system and receiving light at the detector, wherein the light is emitted out of the distal tip of the catheter.

2. The method according to claim 1, further comprising receiving calibration parameters from a user at the laser system.

3. The method according to claim 1, further comprising retrieving catheter specific calibration parameters from a memory.

4. The method according to claim 1, further comprising pulsing the laser with a first pulsing sequence.

5. The method according to claim 1, wherein a portion of the catheter body remains in the package when the at least a portion of the connector is removed from the package.

6. The method according to claim 1, wherein the coupling distal tip step comprises connecting a distal end of the catheter to a channel arranged in the housing.

7. The method according to claim 6, wherein the channel further comprises at least one of flange, detent, ring, or disc configured to secure the distal tip in the channel.

8. A method of calibrating a laser catheter with a laser system, comprising the steps of:
providing the laser catheter, wherein the laser catheter comprises a catheter body, a distal end, a proximal end including a connector, and a fiber optic arranged between at least the proximal end and the distal end;
coupling the connector to the laser system, wherein the distal end of the catheter is coupled in a channel region of a housing coupled to the connector;
positioning the distal tip of the catheter a fixed distance from a light detector disposed within the laser system;
activating the laser system to produce light pulses out of a distal end of the catheter;
receiving the light pulses at the light detector; and comparing energy of the light pulses to a predetermined value and deactivating the laser when the predetermined value has been reached.

9. The method according to claim 8, wherein the predetermined value comprises an energy value in a range from about 5 mJ to about 100 mJ.

10. The method according to claim 8, wherein the predetermined value is stored in memory of the laser system.

11. The method according to claim 8, wherein the predetermined value comprises a look-up table.

12. The method according to claim 8, wherein the step of providing the laser catheter comprises the steps of:
receiving the laser catheter within a sterile package; and
removing at least a portion of the connector from the sterile package.

13. The method according to claim 8, wherein the predetermined value is dependent on at least one of catheter type and medical procedure to be utilized by the laser catheter.

14. A method of calibrating a laser catheter with a laser system, comprising the steps of:
providing the laser catheter, wherein the laser catheter comprises a catheter body, a distal end, a proximal end, a connector, a housing having a first end and a second end, the first end is coupled to the connector and the second end is coupled to a proximal end of the catheter, and a fiber optic arranged between at least the proximal end and the distal end;
coupling the connector to the laser system;
securing the distal end of the catheter to a portion of the housing at a substantially fixed distance from a light detector disposed within the laser system, wherein the distal end of the catheter is optically aligned with the light detector;
providing calibration parameters comprising a calibration threshold value;
calibrating the catheter according to a calibration sequence, wherein the calibrating includes activating the laser system and receiving light emitted out of a distal end of the catheter at the detector and comparing detected light from the detector to the calibration threshold value; and
and stopping the calibration when the calibration threshold value has been detected.

15. The method according to claim 14, wherein the calibration parameters are stored in memory of the laser system.

16. The method according to claim 14, wherein the coupling the connector to the laser system step further comprises detecting the catheter type.

17. The method according to claim 14, wherein the calibration step comprises utilizing a look-up table of pre-entered parameters.

18. The method according to claim 14, wherein the calibration threshold is in a range from about 5 mJ to about 100 mJ.

19. The method according to claim 14, wherein the step of providing the laser catheter comprises the steps of:
receiving the laser catheter within a sterile package; and
removing at least a portion of the connector from the sterile package.

20. A method of calibrating a laser catheter, comprising the steps of:
removing a portion of the laser catheter from a sterile package, wherein the laser catheter comprises a catheter body, a distal end, a proximal end, a connector, a housing having a first end coupled to the connector and a second end coupled to a proximal end of the catheter, and a fiber optic material arranged between at least the proximal end and the distal end of the catheter;
coupling the connector to a laser system;
optically aligning the distal end of the catheter at a substantially fixed distance from a light detector disposed within the laser system;
activating the laser system to produce light pulses out of a distal end of the catheter;
receiving the light pulses at the light detector; and
comparing energy of the light pulses to a predetermined value and deactivating the laser when the predetermined value has been reached.

21. The method according to claim 20, wherein the distal end of the catheter is arranged in a channel region of the housing.

22. The method according to claim 20, wherein coupling the connector to the laser system step further comprises the step of detecting with the laser system a catheter type.

23. The method according to claim 1, wherein coupling the connector to the laser system step further comprises the step of detecting with the laser system a catheter type.

24. A method of calibrating a laser catheter, comprising the steps of:
removing a portion of the laser catheter from a sterile package, wherein the laser catheter comprises a catheter body, a distal end, a proximal end, a connector, a housing including channel region extending from a first end to a second end, the first end of the housing is coupled to the connector, a second end of the housing is coupled to a proximal end of the catheter, and the distal end of the catheter is coupled in at least a portion of the channel, and a fiber optic material is arranged between at least the proximal end and the distal end of the catheter;
coupling the connector to a laser system, wherein the distal end of the catheter is optically aligned with a detector; and
detecting with the laser system a catheter type of the laser catheter.

* * * * *

UNITED STATES PATENT AND TRADEMARK OFFICE
CERTIFICATE OF CORRECTION

PATENT NO. : 8,100,893 B2  Page 1 of 1
APPLICATION NO. : 11/946376
DATED : January 24, 2012
INVENTOR(S) : Tom Dadisman It is certified that error appears in the above-identified patent and that said Letters Patent is hereby corrected as shown below:

Column 7, claim 14, line 42, before "stopping" delete "and".

Signed and Sealed this
First Day of May, 2012

David J. Kappos
*Director of the United States Patent and Trademark Office*